United States Patent
Heckel et al.

(10) Patent No.: US 10,172,665 B2
(45) Date of Patent: Jan. 8, 2019

(54) SYSTEM AND METHOD FOR CONTROLLING OPERATION OF AN ELECTROSURGICAL SYSTEM

(71) Applicant: COVIDIEN LP, Mansfield, MA (US)

(72) Inventors: Donald W. Heckel, Thornton, CO (US); Katherine Wagle, Littleton, CO (US); William D. Faulkner, Boulder, CO (US); Kenneth C. Brockmann, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 635 days.

(21) Appl. No.: 14/851,258

(22) Filed: Sep. 11, 2015

(65) Prior Publication Data

US 2016/0081739 A1 Mar. 24, 2016

Related U.S. Application Data

(60) Provisional application No. 62/052,046, filed on Sep. 18, 2014, provisional application No. 62/052,062, filed on Sep. 18, 2014.

(51) Int. Cl.
*A61B 18/12* (2006.01)
*A61B 18/00* (2006.01)

(52) U.S. Cl.
CPC ...... *A61B 18/1206* (2013.01); *A61B 18/1233* (2013.01); *A61B 2018/0072* (2013.01);
(Continued)

(58) Field of Classification Search
CPC ............ A61B 18/1206; A61B 18/1233; A61B 2018/00642; A61B 2018/00648;
(Continued)

(56) References Cited

U.S. PATENT DOCUMENTS

| 5,318,563 A | 6/1994 | Malis et al. |
| 5,514,129 A | 5/1996 | Smith |

(Continued)

FOREIGN PATENT DOCUMENTS

| CN | 102170834 A | 8/2011 |
| CN | 102170835 A | 8/2011 |
| CN | 103260539 A | 8/2013 |
| EP | 1157667 A2 | 11/2001 |
| EP | 2025297 A2 | 2/2009 |
| EP | 2329782 A1 | 6/2011 |

OTHER PUBLICATIONS

Extended European Search Report from Appl. No. EP 15185747.1 dated Feb. 15, 2016.

(Continued)

*Primary Examiner* — Thomas Giuliani

(57) ABSTRACT

An electrosurgical system including or connected to an output circuitry comprising an electrosurgical device and an electrical cable is modelled during a cable interrogation phase using a transfer matrix in order to determine a leakage capacitance in the electrosurgical system. After the leakage capacitance is assigned or set to a virtual capacitor in the transfer matrix, an output parameter of the electrosurgical system, such as output voltage, output current, output impedance or output electrical power, may be determined by applying an actual input voltage to the output circuitry and measuring a resulting input current, and multiplying the input voltage and measured current by the transfer matrix.

12 Claims, 6 Drawing Sheets

(52) U.S. Cl.
CPC ........ *A61B 2018/00642* (2013.01); *A61B 2018/00666* (2013.01); *A61B 2018/00702* (2013.01); *A61B 2018/00708* (2013.01); *A61B 2018/00755* (2013.01); *A61B 2018/00767* (2013.01); *A61B 2018/00827* (2013.01); *A61B 2018/00875* (2013.01); *A61B 2018/00892* (2013.01); *A61B 2018/00904* (2013.01); *A61B 2018/00928* (2013.01); *A61B 2018/00958* (2013.01)

(58) Field of Classification Search
CPC ........ A61B 2018/00666; A61B 2018/00702; A61B 2018/00767; A61B 2018/0072; A61B 2018/00708; A61B 2018/00755; A61B 2018/00892; A61B 2018/00827; A61B 2018/00875; A61B 2018/00898; A61B 2018/00904; A61B 2018/00928; A61B 2018/00958
USPC ............................ 606/34, 35, 38, 42
See application file for complete search history.

(56) References Cited

U.S. PATENT DOCUMENTS

| | | |
|---|---|---|
| 7,041,096 B2 | 5/2006 | Malis et al. |
| 2006/0224152 A1* | 10/2006 | Behnke .............. A61B 18/1206 606/34 |
| 2009/0254077 A1 | 10/2009 | Craig |
| 2013/0066238 A1 | 3/2013 | Irisawa et al. |
| 2013/0274729 A1 | 10/2013 | Orszulak |
| 2016/0081740 A1* | 3/2016 | Heckel .............. A61B 18/1206 606/34 |

OTHER PUBLICATIONS

Chinese Office Action and English translation issued in Appl. No. CN 201510665431.4 dated Jun. 21, 2017.
Chinese First Office Action and English translation issued in Chinese Application No. CN 201510600348.9 dated Apr. 28, 2017.
Chinese Office Action issued in Appl. No. CN 201510600348.9 dated Dec. 19, 2017, together with English Translation (10 pages).

* cited by examiner

SYSTEM AND METHOD FOR CONTROLLING OPERATION OF AN ELECTROSURGICAL SYSTEM

CROSS REFERENCE TO RELATED APPLICATION

The present application claims the benefit of, and priority to, U.S. Provisional Patent Application Ser. Nos. 62/052,062 and 62/052,046, both of which were filed on Sep. 18, 2014. This application is related to U.S. patent application Ser. No. 14/851,310, filed on Sep. 11, 2015. The entire contents of each of the above applications are hereby incorporated herein by reference.

FIELD OF THE INVENTION

The present disclosure relates to electrosurgical systems. More particularly, the present disclosure is directed to methods for controlling operation of an electrosurgical system during electrosurgical procedures, and to an electrosurgical system that uses the methods.

BACKGROUND

Damaged tissues are sometimes treated using an energy delivering system. Various types of therapeutic energies (e.g., electrical, ultrasonic, microwave, cryogenic, heat, laser, etc.) used in tissue treatment, which are known in the art, may be applied to treat a tissue. Electrosurgery is a tissue treating technique involving delivering of high radio frequency ("RF") electrical energy (e.g., 1-70 watts in auto bipolar electrosurgical systems, 1-300 watts in monopolar electrosurgical systems). Electrosurgery treatment is rendered by an electrosurgical device (e.g., electrosurgical forceps).

Electrosurgical systems conventionally monitor an electrical voltage and an electrical current in order to 'remotely' evaluate the impedance at the electrosurgical device. Evaluation of the impedance at the electrosurgical device enables an electrosurgical system to detect whether the electrosurgical system is in an 'open circuit' state in which the electrosurgical device does not touch the treated site, or in a 'closed circuit' state in which the electrosurgical device touches the treated site. Distinguishing between these two states enables the electrosurgical system to output (generate) therapeutic energy only when the electrosurgical device touches the treated site.

When the surgical device touches a tissue, the impedance evaluated by the electrosurgical system is relatively low (a few tenths of ohms to several thousands of ohms). When the surgical device is detached from a treated tissue, the impedance measured by the electrosurgical system should ideally be infinite (or practically very high; e.g., in the order of tenths of mega ohms). Should this be the case, an impedance gap between the open circuit state and the closed circuit state would have been very large, which would enable the electrosurgical system to distinguish between the two states easily and reliably. However, in practice, the electrosurgical system's periphery, which may include, for example, cable(s), adapter(s), connector(s), surgical device(s), etc., includes parasitic (leakage) impedances that detrimentally affect the impedance gap, that is, they narrow the gap. Depending on the electrical characteristics of the electrosurgical system's periphery, the impedance undesirably imposed by it may vary, for example, from tenths of ohms to tenths of kilo ohms.

The parasitic (e.g., leakage) impedance imposed on the electrosurgical system by its periphery poses a problem which is that the electrosurgical system, which monitors the impedance during electrosurgical procedures, might erroneously interpret a parasitic impedance as an impedance that results from a tissue contact even in cases where the electrosurgical device does not touch the tissue. As a result of this, the electrosurgical system might erroneously continue to deliver therapeutic energy to the electrosurgical device, or resume delivery of the therapeutic energy, even though the device (e.g., forceps) is not touching the surgical site. Holding the treatment device by a surgeon may also add parasitic impedance, which exacerbates the problem of misinterpretation of the impedance evaluated by the electrosurgical system. (The surgeon may hold the device prior to treatment and then during treatment, and, occasionally, s/he may detach it from the treated tissue and, therefore, a parasitic impedance caused by the surgeon might change during the electrosurgical process as well.)

Because, conventionally, the electrical voltage and current that the electrosurgical system uses to evaluate the impedance at the electrosurgical device, hence the device-tissue contact degree, do not genuinely represent the real impedance at the electrosurgical device (due to the aforesaid parasitic/leakage capacitances), not only that distinguishing between the open circuit state and the closed circuit state might not be reliable, the electrosurgical system might deliver/output therapeutic/treatment energy to the tissue which is not therapeutically optimal.

It would be beneficial to have a method and system that enable reliable operation of an electrosurgical system despite unknown impedance changes in the electrosurgical system during electrosurgical procedures.

SUMMARY

A method of operating an electrosurgical system, which may be connected to an output circuitry including an electrical cable connected to an electrosurgical device, may include defining a transfer matrix that electrically represents the output circuitry and includes a virtual capacitor (Cvirtual) to represent a leakage capacitance (Clkg) in the output circuitry. The method may include assigning or setting, to the virtual capacitor, a capacitance value that may represent the leakage capacitance. The capacitance value may be known in advance (e.g., it may be read from a device selected from the group consisting of RFID tag and barcode, and set to Cvirtual automatically, or it may be set manually, by receiving an input from a user.). The capacitance value may not be known in advance, in which case it may be determined by sweeping the value of the virtual capacitor to determine an optimal capacitance, which is a virtual/theoretical capacitance that best represents the leakage capacitance. (By 'a virtual/theoretical capacitance that best represents the leakage capacitance' is meant a virtual/theoretical capacitance whose value may be identical to, or approximately the same as, the value of the leakage capacitance.)

The method may, during an electrosurgical procedure, also include (i) applying, by the electrosurgical system, an input voltage (Vin) to an (e.g., input end of) the electrical cable, and measuring an input current (Iin) in the electrical cable in response to the input voltage, Vin; (ii) calculating an output impedance (Zout) of the output circuitry from the input voltage (Vin) and the input current (Iin) using the transfer matrix, and (iii) comparing the output impedance (Zout) to an impedance threshold value. A determination as to a current, or next, operation mode of the electrosurgical system may be based on the comparison result.

Calculating the output impedance (Zout) of the electrical cable may include calculating, by using the transfer matrix, an output voltage (Vout) and an output current (Iout) for the output circuitry from the input voltage (Vin) and from the input current (Iin). The output voltage (Vout) and the output current (Iout) calculated for the output circuitry may be used to calculate an electrical power (Pout) that is delivered to a bodily organ or tissue from the electrosurgical system via the electrosurgical device.

Assigning the optimal capacitance value to the virtual capacitor (Cvirtual) may include, during a cable interrogation phase, (i) changing the value of the virtual capacitor across a series of capacitance values and calculating, by using the transfer matrix representative of the output circuitry, a series of output impedances respectively corresponding to the series of capacitance values; (ii) deriving a maximum output impedance (Zmax) from the series of output impedances; (iii) determining an optimal capacitance value for the virtual capacitor for which the output impedance is maximal; and (iv) assigning the optimal capacitance value to the virtual capacitor. The value of the virtual capacitor (Cvirtual) may be changed (swept) according to a capacitance interval, for example it may be swept within a capacitance range 50 pF-600 pF. (Other capacitance ranges may be used.)

Assigning the optimal capacitance value to the virtual capacitor may include disconnecting the electrosurgical device from the electrical cable, then applying, by the electrosurgical system, an input voltage (Vin) to the electrical cable and measuring an input current (Iin) in the electrical cable in response to the applied input voltage (Vin) and, for each value of the virtual capacitor, multiplying the input voltage (Vin) and the input current (Iin) by the transfer matrix to obtain an output voltage (Vout) and an output current (Iout) for the output circuitry, and calculating an output impedance (Zout) of the output circuitry from the output voltage (Vout) and the output current (Iout). The maximum output impedance (Zmax) may be selected from the series of output impedances, or it may be interpolated from the series of output impedances.

Determining an operation mode of the electrosurgical system may include determining whether the electrosurgical device is connected to, or disconnected from, the electrical cable, and/or determining whether the electrosurgical device touches a bodily organ or tissue, and/or the electrical cable is connected to, or disconnected from, the electrosurgical system, and/or determining, based on the comparison result, whether the output circuitry is in an "open circuit" state in which the electrosurgical device does not touch a bodily organ or tissue, or in a "closed circuit" state in which the electrosurgical device touches the bodily organ or tissue.

The method as in claim 1, wherein the output circuitry of the electrosurgical system comprises any of: (i) the electrical cable connected to the electrosurgical system, (ii) the electrosurgical device touches a bodily organ or tissue, (iii) an adapter connecting the electrical cable to the electrosurgical system, (iv) an adapter connecting the electrosurgical device to the cable, and (v) the electrosurgical device is held by a user, and including any combination thereof.

According to another embodiment, a method of operating an electrosurgical system, which includes a signal generator and an output circuitry comprising an electrical cable connecting an electrosurgical device to the electrosurgical system, may include (i) applying an input voltage (Vin) to the electrical cable and measuring an input current (Iin) in the electrical cable in response to the input voltage, Vin, (ii) calculating an electrical parameter of the output circuitry from the input voltage (Vin) and the input current (Iin) and by using a transfer matrix electrically representing the output circuitry. An operation mode for the electrosurgical system, or to which the electrosurgical system is to transition, may be determined based on the value of the electrical parameter.

The transfer matrix may include a virtual capacitor (Cvirtual), and the method may include assigning or setting to the virtual capacitor (Cvirtual) a capacitance value that represents a leakage capacitance (Clkg) in the output circuitry. The leakage capacitance (Clkg) may include one or more of: a leakage capacitance due to the cable, a leakage capacitance due to the electrosurgical device, a leakage capacitance due to a connector connecting the cable to the electrosurgical system, a leakage capacitance due to a connector connecting the cable to the electrosurgical device, and a leakage capacitance due to a subject (e.g., surgeon, technician, etc.) touching the electrosurgical device.

Assigning the capacitance value representative of the leakage capacitance (Clkg) to the virtual capacitor (Cvirtual) may include assigning or setting a value of the leakage capacitance (Clkg) to the virtual capacitor (Cvirtual). Alternatively, assigning the capacitance value representing the leakage capacitance (Clkg) to the virtual capacitor (Cvirtual) may include, during a cable interrogation phase, (i) changing the value of the virtual capacitor (Cvirtual) of the transfer matrix across a series of capacitance values and calculating, by using the transfer matrix, for the output circuitry, a series of output impedances respectively corresponding to the series of capacitance values; (ii) deriving a maximum output impedance (Zmax) from the series of output impedances; (iii) determining an optimal capacitance value for which the output impedance is maximal (Zmax); and (iv) assigning the optimal capacitance value to the virtual capacitor (Cvirtual).

The operation mode may be selected from the group consisting of: (i) delivering, by/from the signal generator, via the electrosurgical device, a therapeutic energy to a treated site, (ii) adjusting an electrical parameter of the signal generator when or while the therapeutic energy is delivered to the treated site, and (ii) refraining from delivering therapeutic energy to the treated site.

The electrical parameter may be an output impedance (Zout) of the output circuitry, and the method may include determining, based on a value of the output impedance (Zout), the operation mode of or for the electrosurgical system and/or distinguishing between an 'open circuit' state of the output circuitry in which the electrosurgical device is detached from a treated site, and a 'closed circuit' state of the output circuitry in which the electrosurgical device is attached to (touches) the treated site. Calculating the output impedance (Zout) of the output circuitry may include calculating an output voltage (Vout) and an output current (Iout) of the output circuitry by multiplying Vin and Iin by the transfer matrix. The electrical parameter may be an output electrical power (Pout) that is delivered or to be delivered to a treated site via the electrosurgical device. Calculating the output electrical power may include calculating an output voltage (Vout) and an output current (Iout) of the output circuitry by multiplying Vin and Iin by the transfer matrix. The method may include controlling the output electrical power to provide an optimal therapeutic energy to the treated site during therapeutic energy delivery.

Also provided is an electrosurgical system that may include a therapeutic energy delivering generator, a controller to control the therapeutic energy generator, and an output circuitry. The output circuitry may include, for example, an electrosurgical device to transfer therapeutic energy to a treated site, and an electrical cable that may electrically connect the electrosurgical device to the electrosurgical system.

The controller may be configured to define a transfer matrix that electrically represents the electrosurgical system, or the output circuitry. The transfer matrix may include a virtual capacitor (Cvirtual) for representing a leakage capacitance (Clkg) in the electrosurgical system, or in the output circuitry. The controller may be configured to assign, to the virtual capacitor (Cvirtual), a capacitance value that may represent the leakage capacitance (Clkg), and to monitor an electrical parameter of the output circuitry by (i) applying an input voltage (Vin) to the electrical cable and measuring an input current (Iin) in the electrical cable, and (ii) calculating an electrical parameter of the output circuitry from the input voltage (Vin) and the input current (Iin) and by using the transfer matrix. The controller may be configured to determine an operation mode of or for the electrosurgical system based on the value of the electrical parameter.

The electrical parameter may be selected from the group consisting of: output voltage of the output circuitry, output current of the output circuitry, output impedance and output electrical power delivered to the treated site. The operation mode may be selected from the group consisting of: (i) delivering, from the signal generator, therapeutic energy to a treated site, (ii) adjusting an electrical parameter of the signal generator when the therapeutic energy is delivered to the treated site, and (ii) refraining from delivering therapeutic energy to the treated site.

The controller may be configured to receive a capacitance value (if it is known in advance) that represents the leakage capacitance in the output circuitry, and to assign or set this value to the virtual capacitance. If the capacitance value representing the leakage capacitance is unknown, the controller may be configured to evaluate it by changing ('sweeping') the value of the virtual capacitor (Cvirtual) in the transfer matrix across a series of capacitance values, and calculating, by using the transfer matrix, for the output circuitry, a series of output impedances respectively corresponding to the series of capacitance values. Then, the controller may derive a maximum output impedance (Zmax) from the series of output impedances, and determine (e.g., calculate) an optimal capacitance value for which the output impedance is maximal (Zmax). Then, the controller may assign or set the optimal capacitance value to the virtual capacitor (Cvirtual).

The controller may determine the capacitance value representing the leakage capacitance (Clkg) to the virtual capacitor (Cvirtual) by (i) changing the value of the virtual capacitor (Cvirtual) of the transfer matrix across a series of capacitance values and calculating, by using the transfer matrix, for the output circuitry, a series of output impedances respectively corresponding to the series of capacitance values, (ii) deriving a maximum output impedance (Zmax) from the series of output impedances, and (iii) determining an optimal capacitance value for the virtual capacitor (Cvirtual) for which the output impedance is maximal (Zmax).

The controller may, while the electrosurgical device is detached from the treated site (e.g., during a cable interrogation phase), cause the signal generator to output an input voltage (Vin) to the electrical cable, and to measure an input current (Iin) in the electrical cable in response to the input voltage (Vin), and, for each value of the virtual capacitor (Cvirtual) the controller may multiply the input voltage (Vin) and the input current (Iin) by the transfer matrix to obtain an output voltage (Vout) and an output current (Iout) of the output circuitry. Then, the controller may calculate, for each value of the virtual capacitor (hence for each transfer matrix having a different value of Cvirtual), an output impedance (Zout) of the output circuitry from the pertinent output voltage and output current.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining", "analyzing", "checking", or the like, may refer to operation(s) and/or process(es) of a computer, a computing system or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not limited to a particular order or sequence. Additionally, some of the described method embodiments or steps thereof can, for example, occur or be performed at the same point in time.

Figure 1A:
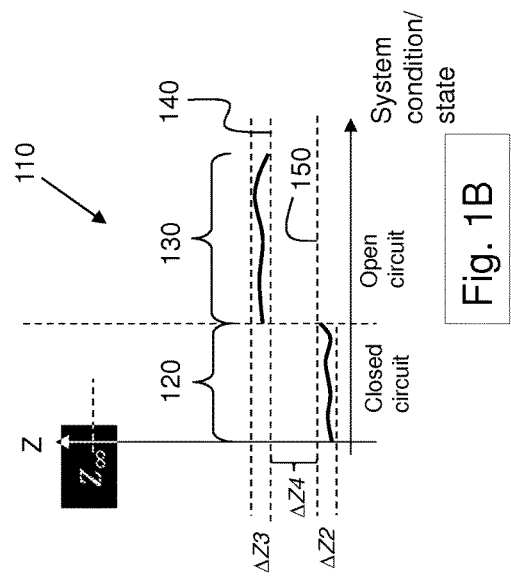
FIG. 1A shows a plot illustrating an ideal situation in the context of auto bipolar electrosurgical systems.

FIG. 1A shows a plot 100 illustrating an ideal situation in the context of an autobipolar ("ABP") electrosurgical system. The horizontal axis indicates a state/condition of the ABP electrosurgical system; e.g., system's output circuit is closed versus open. The vertical axis indicates an external output impedance to be sensed by the ABP electrosurgical system at the tip of the electrosurgical device. (The same applies to the axes in FIG. 1B, which is described below.)

When an electrosurgical system performs an electrosurgical procedure, the electrosurgical (treatment) device (e.g., forceps) performing the treatment may, at some instants, touch the treated bodily organ or tissue, and at other instants it may be intentionally moved away from the treatment site, for example, in order not to provide too much energy to the treated tissue/site, for example in order not to overheat the treated tissue/site. (The treatment may, at times, be unintentionally moved away from the treatment site.)

In ideal cases, when the treatment device touches the treated tissue (e.g., when the ABP system's electrical circuitry (the electrosurgical system's 'output circuitry', or 'output circuitry' for short) is closed via the tissue's impedance), the ABP system would sense a relatively small impedance (Z1, FIG. 1A), which is approximately the impedance of the tissue, and when the treatment device does not touch the treated tissue (i.e., when the ABP system's output circuitry is open), the impedance that the ABP system would sense should theoretically be infinite ($Z_\infty$, FIG. 1A), or, in practice, at least in the order of hundreds of mega ohms.

As shown in FIG. 1A, the impedance gap ΔZ1 (FIG. 1A) between Z1 (the impedance during the 'closed circuit' state) the $Z_\infty$ (the impedance during the 'open circuit' state) is very large so that the two distinct impedance states can be distinguished easily. Since the ABP system should stop delivering therapeutic RF energy when the treatment device is moved away from the body, the ability to reliably distinguish between the two impedance states (i.e., Z1 versus $Z_\infty$) is prerequisite to safe reliable and efficient operation of the electrosurgical system. However, in practice, the impedance gap is far from being ideal, in part due to the parasitic capacitances existing in the output circuitry of the electrosurgical system (and also in the electrosurgical system itself), as demonstrated in FIG. 1B, which is described below.

Figure 1B:
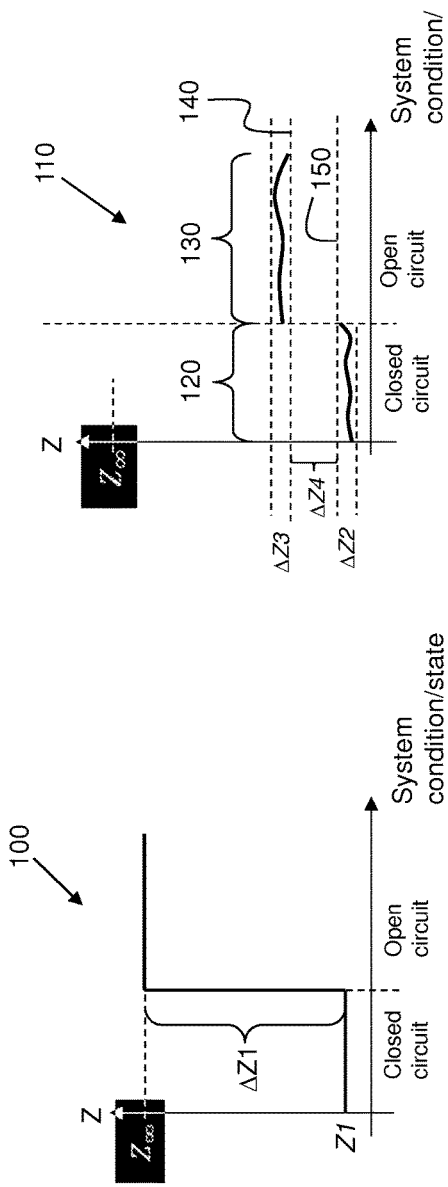
FIG. 1B shows a plot illustrating realistic situations in the context of autobipolar systems.

FIG. 1B shows a plot 110 illustrating example situations in the context of an ABP system. When the treatment device (e.g., forceps) touches a treated tissue, see device condition 120; i.e., when the ABP system's output circuitry is closed via the tissue's impedance, the ABP system typically senses a relatively small impedance (under line 150) that may change, for example, according to changes in the physiological properties of the tissue, for example, while the tissue is treated. Regardless of whether the ABP system's output circuitry is closed or open, the system/equipment setting, which typically includes cables, flying lead(s), adapter(s), etc., introduces a parasitic impedance that lowers the total impedance sensed by the ABP system. So, the impedance variations in system condition 120 ('closed circuit')) also reflect this impact. As shown in FIG. 1B, the impedance in the 'closed circuit' state (120) may vary within ΔZ2, which can be within the range of tenths of ohms to kilo ohms, for example. A low pass filter may be used to remove high frequency components from the impedance measurements in order to obtain a smoother impedance signal or data during closed circuit state 120.

When the treatment device stops touching the treated site, causing the ABP system's output circuitry to open (system condition 130), the output impedance that the ABP system typically senses in 'open circuit' state 130 is higher than the impedances usually sensed by the ABP system in the 'closed circuit' state (120), but still, it is much lower than desired because of the parasitic impedance imposed on the system's output circuitry by the periphery equipment setting. A low pass filter may be used to remove high frequency components in order to obtain a smoother impedance signal or data during open circuit state 130.

The parasitic impedance may, at least at times, be in the same or similar order as the tissue impedance, thus making distinguishing between the 'closed circuit' state and the 'open circuit' state difficult, and sometimes even impossible. As shown in FIG. 1B, the impedance variations in the 'open circuit' state (130) can have a magnitude that may be as large as ΔZ3, which can be within the range of tenths of kilo ohms.

As shown in FIG. 1B, the 'in-between state' impedance gap ΔZ4 between the minimum 'open circuit' impedance (140) and the maximum 'closed circuit' impedance (150) is much smaller than ΔZ1 (FIG. 1A) (Z1<<ΔZ1; ΔZ1→∞), and it may not enable the ABP system to reliably distinguish between the two impedance states. Due to the parasitic impedance cause by the equipment setting, an open circuit impedance may resemble (e.g., have a value characterizing) a closed circuit impedance, in which case the ABP system might erroneously determine that the circuit is closed, rather than open, leading to a wrong conclusion that delivery of therapeutic RF energy should be continued or resumed even though the therapeutic device no longer touches the treated site. Because impedance gap ΔZ4 is relatively small, it is essential, for proper operation and optimal results, that the output impedance of the electrosurgical system's output circuitry be accurately and reliably calculated during the entire electrosurgical procedure, in order for the electrosurgical system to deliver an optimal electrical energy to the treated organ or tissue whenever it is required (e.g., during closed circuit state).

The present disclosure discloses a method and system for accurately and reliably calculating the output impedance of the electrosurgical system's output circuitry. Briefly, the output circuitry of the electrosurgical system is modelled to a two-port circuit, and a transfer matrix representing the two-port circuit is used in two phases: (1) cable interrogation phase, during which the overall parasitic capacitance imposed on the electrosurgical system's output circuitry is determined, and (2) impedance monitoring phase, during which the value of the overall parasitic capacitance determined in the first phase is assigned to the transfer matrix, and the transfer matrix is used to calculate the output impedance of the electrosurgical system's output circuitry. (The overall parasitic capacitance imposed on the electrosurgical system's output circuitry is referred to herein as "leakage capacitance" (Clkg.)

Figure 2A:
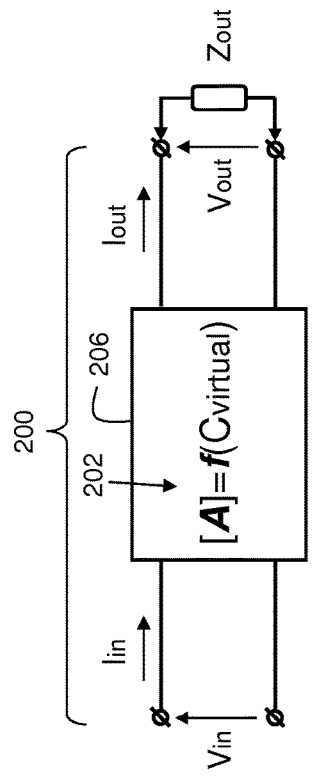
FIG. 2A shows a conceptual two-port network in according to an example embodiment.

FIG. 2A shows a conceptual two-port network 200 in accordance with the present invention. Two-port network 200 may electrically represent an electrosurgical system. Network 200 may include an electrical circuit (206). Electrical circuit 206 may include circuit elements that may include serial and parallel impedances of an electrosurgical system represented by network 200, or of an output circuitry of the electrosurgical system. Some of the impedances may represent intrinsic (e.g., internal) impedances of the electrosurgical system. Other impedances (e.g., extrinsic impedances) may represent impedances of periphery device(s) that may be or include cable(s), connector(s), adapter(s) and an electrosurgical/therapeutic device(s) (e.g., forceps). The periphery devices may be connected to the electrosurgical system, for example during an electrosurgical procedure, and thus be or make the electrosurgical system's output circuitry. Some of the impedances of, or included in, two-port network 200 may represent, or caused by, parasitic capacitances that undesirably leak electrical current. Network 200 may represent a two-port circuit similar to, for example, an autobipolar (ABP) type electrosurgical system, or it may represent a two-port circuit that is used by an autobipolar type electrosurgical system to distinguish between various states or conditions of the electrosurgical system, for example the system's open circuit state and closed circuit state.

A transfer matrix A (202) may be defined, or formed, to represent two-port network 200. Transfer matrix 202 may be defined or formed, for example, based on or from the intrinsic impedances and extrinsic impedances mentioned above. (That is, transfer matrix A may be described as [A]=f(Zsrc_Int, Zlkg_Int, Zsrc_Ext, Cvirtual), where Zsrc_Int, Zlkg_Int and Zsrc_Ext are the internal and external impedances mentioned above, and Cvirtual is further discussed below.) Transfer matrix A may be defined such that it includes a virtual (e.g., software implemented) capacitor, Cvirtual, whose capacitance value may represent the overall parasitic/leakage capacitance value, Clkg, in network 200, or whose value may be 'swept' to determine the network's parasitic/leakage capacitance value, Clkg. Once defined or formed, transfer matrix A (202) may be used as shown at formulae (1) and (2), where coefficient $A_{11}$ is defined as $A_{11}$=Vin/Vout (for Iout=0), coefficient $A_{12}$ is defined as $A_{12}$=Vin/Iout (for Vout=0), coefficient $A_{21}$ is defined as $A_{21}$=Iin/Vout (for Iout=0), and coefficient $A_{22}$ is defined as $A_{22}$=Iin/Iout (for Vout=0). (Vin, Iin, Vout and Iout are shown in FIG. 2A.)

$$Vin = A_{11} * Vout + A_{12} * (Iout) \quad (1)$$

$$Iin = A_{21} * Vout + A_{22} * (Iout) \quad (2)$$

... or put differently–

$$\begin{bmatrix} Vin \\ Iin \end{bmatrix} = [A] * \begin{bmatrix} Vout \\ Iout \end{bmatrix} \quad (3)$$

The output impedance (Zout) of network 200 may be calculated using formula (4).

$$Zout = Vout/Iout \quad (4)$$

Vout and Iout may be found by inverting transfer matrix A and multiplying the resulting transfer matrix B by Vin and Iin, as shown at formula (5):

$$\begin{bmatrix} Vout \\ Iout \end{bmatrix} = [B] * \begin{bmatrix} Vin \\ Iin \end{bmatrix} \quad (5)$$

where $B=A^{-1}$ ($A^{-1}$ is the inversion of transfer matrix A).

Assuming that transfer matrix B includes, or factors in, the all the parasitic/leakage capacitances, Clkg, existing in two-port network 200; that is, assuming that Cvirtual=Clkg (assuming Clkg is pre-known), the two-port network's output voltage (Vout) and output current (Iout) can directly and easily be calculated for any actual input voltage (Vin) and input current (Iin), because when Cvirtual=Clkg, transfer matrix A, and therefore transfer matrix B, genuinely represents the electrical circuit of network 200. To that extent, an actual input voltage (Vin) can be provided to network 200, and a corresponding input current (Iin) may be measured in response to voltage Vin. (Iin is a function of Clkg, which is the actual leakage capacitance in network 200's circuitry.) Then, the network's output impedance (Zout) can be calculated from Vout and Iout.

Vout and Iout can, allegedly, be measured by using a voltmeter and a current meter. However, using such meters in electrosurgical environment would necessitate additional cabling, and this may be problematic, for example, because these cables may have to be handled (e.g., moved around) and they may add leakage capacitance of their own. Using the output impedance calculation method disclosed herein renders such meters and cabling unnecessary.

The parasitic/leakage capacitance 'contribution of the cable (which is included in electrosurgical system's output circuitry) to the overall parasitic/leakage capacitance Clkg may be known in advance. For example, it may be read from a barcode or an RFID tag and the read value may be input/added to transfer matrix B; i.e., assigned to Cvirtual. Since a capacitance per unit of length of a standard cable can usually be found in a specification sheet, this information and knowing the cable's length enables determining the contribution of the cable to the overall parasitic capacitance, Clkg. However, there may be cases where the cable's parasitic capacitance is unknown, and even when it is known, 'contribution' of the other parts of network 200 (e.g., electrosurgical system) may be unknown.

In order to find the value of Clkg, a series of theoretical (e.g., virtual, software implemented) capacitance values may be assigned/set to Cvirtual, for example one capacitance value at a time, and a corresponding output impedance, Zout, may be calculated for each theoretical/software capacitance value by using formula (5). Then, a maximum output impedance, Zmax, may be searched for in, or selected or derived from, the group, or series, of the calculated output impedances. The value of the overall parasitic capacitance Clkg resulting in Zmax may be set/assigned to the software implemented virtual capacitor, Cvirtual. The way Zmax and Clkg are determined/found is described below in more detail.

By way of example, the value of Cvirtual may be set to a first capacitance value C1 (e.g., C1=50 pF), and a matrix B(1), which is the matrix B corresponding to (factoring in) the first capacitance value (C1), may be calculated with the capacitance value 50 pF factored in. Then, an interrogation input voltage Vin (Vin, FIG. 2A) may be applied to the circuit, and an input current Iin(1) (Iin, FIG. 2A) may be measured for Vin, thus for C1. Then, knowing matrix B(1) and the related voltage-current pair {Vin, Iin(1)}, Vout(1) and Iout(1) may be calculated by using formula (5). Then, a corresponding output impedance Zout(1) may be calculated by dividing voltage Vout(1) by current Iout(1) (i.e., Zout(1)=Vout(1)/Iout(1)). Then, the value of Cvirtual may be set to a second capacitance value C2 (e.g., C2=60 pF) and a matrix B(2), which is the matrix B corresponding to C2, may be calculated, this time with the capacitance value 60 pF factored in. Then, the same interrogation input voltage (Vin, FIG. 2A) may be applied to the circuit, and a current Iin(2), which is current Iin measured for C2, may be measured. Then, knowing matrix B(2) and the related voltage-current pair {Vin, Iin(2)}, Vout(2) and Iout(2) may be calculated by using formula (5). Then, a corresponding circuit output impedance, Zout(2), may be calculated by dividing voltage Vout by current Iout(2) (i.e., Zout(2)=Vout (2)/Iout(2)). The same process may be repeated or iterated as many times as required or desired, to thereby obtain a series of output impedances from which, or based on which, the maximum output impedance, Zmax, may be determined.

Then, the capacitance, Cvirtual, resulting in, or corresponding to, the maximum output impedance, Zmax, may be determined.

Transfer matrix A (and, therefore matrix B) may be devised such that, during sweeping of the capacitance value of Cvirtual, for example in the range of 50 pF-600 pF, the maximum output impedance, Zmax, occurs when the value of Cvirtual matches that of the overall parasitic capacitance, Clkg, of network 200; i.e., when Cvirtual=Clkg. Cvirtual=Clkg occurs when Zout=Zmax because the system's model, as embodied in the transfer matrix, is closest to being correct when Zout has the highest value. Every output impedance, Zout, is calculated for an open circuit condition in order for the measured input current, Iin, which is an actual electrical current, to reflect or represent the electrical current leaked by the leakage capacitance, without having any electrical load affecting this current. The higher the output impedance, Zout, calculated for any particular virtual impedance ($-1/jwC_{virtual}$) inserted into the model (e.g., transfer matrix), the closer the particular virtual impedance is to the actual cable's impedance, and, therefore, the closer the value of the virtual capacitance is to that of the leakage capacitance.

Figure 2B:
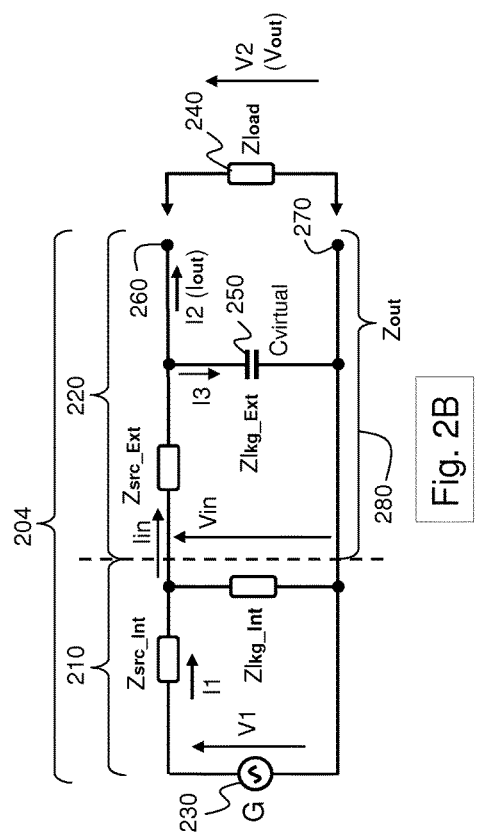
FIG. 2B schematically illustrates a two-port network representing an electrosurgical system according to an example embodiment.

FIG. 2B schematically illustrates a two-port network 204 according to an example embodiment. Two-port network 204 may electrically represent (e.g., model) an electrosurgical system. Complex impedances Zsrc_Int and Zlkg_Int may represent intrinsic parasitic (leakage) complex impedances inside an electrosurgical system (e.g., system 400 of FIG. 4). Complex impedances Zsrc_Ext and Zlkg_Ext may represent extrinsic parasitic complex impedances of, caused by or associated with, a periphery system, which is referred to herein as the "output circuitry", that may be connected to the electrosurgical system (e.g., output circuitry 420). (The term 'output circuitry' may refer to or include any device, apparatus or system that is, or can be, electrically connected to (e.g., plugged into) an electrosurgical system, via/through which the electrosurgical system delivers, or may deliver, 'interrogation' signals during an impedance monitoring phase, or therapeutic energy to a treated site during electrosurgical procedure.) Two-port network 204 may be analyzed as two sub networks: sub network 210 and sub network 220. Each sub network may likewise be analyzed, for example as described below. In connection with FIG. 2B, unless specifically stated otherwise, an output voltage and an output current are voltage and current at the output of the discussed sub network. For example, a voltage that may be regarded as input voltage of/for sub network 220, is an output voltage for sub network 210.

Impedance Zload may represent an impedance of a treated site (e.g., tissue) during electrosurgical procedure. Impedance Zlkg_Ext may represent an overall parasitic (leakage) capacitance, Clkg, of network 204 or sub network 220, which leaks current I3. Ideally, Iin=0 when Clkg=0 pF and the electrosurgical device does not touch a tissue. However, since the impedance due to the leakage capacitance (i.e., Xc=($-1/jwC$)) might, at times, resemble impedance Zload (the impedance of the tissue), for example it may have a value in the same order as impedance Zload, there is some non-zero current (I3>0 Amp) that leaks via the leakage capacitance, and since Iin=I2+I3=I3, knowing only the value of current Iin may not suffice to decisively determine the correct value of the system's output impedance and, therefore, and it may not suffice to distinguish between the 'open circuit' state and the 'closed circuit' state of network 204 or network 220.

Assuming output voltage V2 and output current I2 of a two-port network are known, an input voltage V1 and an input current I1 may be calculated using equations (6) and (7), where $A_{11}$ and $A_{22}$ are dimensionless coefficients, $A_{12}$ is impedance and $A_{21}$ is admittance. The four coefficients may be calculated using the definitions specified above in connection with formulae (1) and (2).

$$V1 = A_{11}V2 + A_{12}(-I2) \tag{6}$$

$$I1 = A_{21}V2 + A_{22}(-I2) \tag{7}$$

A total impedance, Ztotal (also referred to as Zout 280), may be calculated using formula (8):

$$Ztotal = Zsrc + \frac{Zlkg \cdot ZLoad}{Zlkg + ZLoad} \tag{8}$$

Voltage Vin at the input of circuit 220 may be calculated using formula (9):

$$Vin = \frac{Iin \cdot (Zlkg \cdot Zsrc + Zlkg \cdot ZLoad + Zsrc \cdot ZLoad)}{Zlk + ZLoad} \tag{9}$$

Accordingly, current I1 (I1=Iin) may be calculated using formula (10):

$$I1 = \frac{Vin \cdot (Zlkg + ZLoad)}{Zlkg \cdot Zsrc + Zlkg \cdot ZLoad + Zsrc \cdot ZLoad} \tag{10}$$

The output voltage (Vout) on Zload (Vout=V2) may be calculated using formula (11) below, and the current (Iout) through Zload (Iout=I2) may be calculated using formula (12) below.

$$Vout = \frac{Vin \cdot Zlkg \cdot ZLoad}{Zlkg \cdot Zsrc + Zlkg \cdot ZLoad + Zsrc \cdot ZLoad} \tag{11}$$

$$Iout = \frac{Vin \cdot Zlkg}{Zlkg \cdot Zsrc + Zlkg \cdot ZLoad + Zsrc \cdot ZLoad} \tag{12}$$

Using the equations and the coefficient definitions above, and assuming that Zload is infinite (because the circuit analysis performed during a cable interrogation phase, which is described in more detail below, is performed when the electrosurgical system is in an open circuit state), the resulting matrix coefficients $A_{11}$, $A_{12}$, $A_{21}$ and $A_{22}$ are:

$$A11 = \frac{Zsrc}{Zlkg} + 1 \tag{13}$$

$$A12 = Zsrc \tag{14}$$

$$A21 = \frac{1}{Zlkg} \tag{15}$$

$$A22 = 1 \tag{16}$$

A corresponding transfer matrix Aint would, therefore, be as shown below (17).

$$Aint = \begin{pmatrix} \frac{Zsrc}{Zlkg} + 1 & Zsrc \\ \frac{1}{Zlkg} & 1 \end{pmatrix} \quad (17)$$

Coefficients $A_{11}$ and $A_{21}$ of matrix Aint are a function of the value of a corresponding leakage impedance Zlkg. ('int' in 'Aint' means 'internal', which means "in the electrosurgical system itself".) This enables calculating the circuit's output voltage and output current with the effect of a parasitic capacitance factored in.

According to transmission matrix theory, A*[out]=[in]. (Input parameters, [in], are equal to output parameters, [out], multiplied by matrix A.) To calculate the circuit output [out], matrix Aint is inverted, $Aint^{-1}=B$, so that B*[in]=[out]. This enables calculating the output voltage and the output current of the circuit from the input voltage and input current, assuming that transfer matrix B is known.

Inverting matrix Aint above results in matrix Bint ($Bint=Aint^{-1}$) (18) below.

$$Bint = \begin{pmatrix} 1 & -Zsrc \\ -\frac{1}{Zlkg} & \frac{Zlkg + Zsrc}{Zlkg} \end{pmatrix} \quad (18)$$

The output voltage, Vout, and the output current, Iout, at the load are function of the input voltage (Vin) and the input current (Iin) multiplied by matrix B, as shown in formula (19).

$$B \text{ matrix}*V/I \text{ in}=V/I \text{ out} \quad (19)$$

Therefore, the output voltage, Vout, and the output current, Iout, can be calculated by multiplying matrix B by Vin and Iin, as shown in formula (20).

$$Out := \begin{pmatrix} 1 & -Zsrc \\ -\frac{1}{Zlkg} & \frac{Zlkg + Zsrc}{Zlkg} \end{pmatrix} \cdot \begin{pmatrix} Vi \\ Ii \end{pmatrix} \quad (20)$$

In order to find (and later use) a single matrix B (Ball) for the entire circuit (e.g., for entire network 204) that will combine (factor in) the impedance (e.g., parasitic capacitance) effect of both the sub network 210 and sub network 220, a matrix Bint corresponding to circuit 210 is to be multiplied by a matrix Bext corresponding to circuit 220; i.e., an overall matrix, Ball, may be found such that Ball=Bext*Bint. To do that, the matrices Bext and Bint have to be found. Matrix Bint is the same as matrix B in equation (20) above except that 'B' changes to 'Bint', 'Zsrc' changes to 'ZsrcInt' and 'Zlkg' changes to 'ZlkgInt', as shown at formula (21) below.

$$Bint := \begin{pmatrix} 1 & -ZsrcInt \\ -\frac{1}{ZlkgInt} & \frac{ZlkgInt + ZsrcInt}{ZlkgInt} \end{pmatrix} \quad (21)$$

The internal source impedance ('ZsrcInt') and internal leakage impedance ('ZlkgInt') of matrix Bint, which are referred to as "internal cable compensation", may be determined during calibration of the electrosurgical system, and since these values do not change significantly during electrosurgical procedure and from one electrosurgical procedure to another, they can be hardcoded into the electrosurgical system's software. (The electrical parameters of the internal cable compensation typically depend on the cable layout and the printed circuit board (PCB) layout internal to the electrosurgical system, and they are determined per type of electrosurgical generator.)

Matrix Bext is the same as matrix B in equation (20) above except that 'Bint' changes to 'Bext', 'Zsrc' is changed to 'ZsrcExt' and 'Zlkg' is changed to 'ZlkgExt', as shown at formula (22) below.

$$Bext := \begin{pmatrix} 1 & -ZsrcExt \\ -\frac{1}{ZlkgExt} & \frac{ZlkgExt + ZsrcExt}{ZlkgExt} \end{pmatrix} \quad (22)$$

Accordingly, the overall matrix B (Ball) corresponding to circuit 204 is as shown below (formula 23):

$$B = B_{ext} \cdot B_{int} = \begin{bmatrix} B_{11} & B_{12} \\ B_{21} & B_{22} \end{bmatrix} \quad (23)$$

where, $$B_{11} = \frac{Z_{srcExt}}{Z_{lkgInt}} + 1$$

$$B_{12} = -\left(Z_{srcInt} + \frac{Z_{srcExt}(Z_{lkgInt} + Z_{srcInt})}{Z_{lkgInt}}\right)$$

$$B_{21} = -\left(\frac{1}{Z_{lkgExt}} + \frac{Z_{lkgExt} + Z_{srcExt}}{Z_{lkgInt} Z_{lkgExt}}\right)$$

and, $$B_{22} = \frac{Z_{srcInt}}{Z_{lkgExt}} + \frac{(Z_{lkgInt} + Z_{srcInt})(Z_{lkgExt} + Z_{srcExt})}{Z_{lkgInt} Z_{lkgExt}}$$

As shown above, matrix B (formula (23) above) includes four variables: (1) ZsrcInt, (2) ZlkgInt, (3) ZsrcExt, and (4) ZlkgExt. (Zload in Matrix B is infinite in order to represent an 'open circuit' state.) Variables ZsrcInt, ZlkgInt and ZsrcExt of matrix B are relatively constant (and known) per used electrosurgical system and periphery equipment. Variable ZlkgExt represents a virtual capacitor (e.g., Cvirtual 250, FIG. 2B) that is added to the transfer matrix in order to represent the leakage capacitance of an output circuitry (e.g., output circuitry 220) that is, or may be, connected to the electrosurgical system.

If the value of the (total) leakage capacitance of electrosurgical system 204, or of output circuitry 220, is known (whether in advance, or after manipulation of the value of Cvirtual), it may be added to a transfer matrix such as transfer matrix B. That is, the known leakage capacitance value may be assigned or set to the virtual capacitor, Cvirtual (shown at 250), and the transfer matrix, with the leakage capacitance value assigned/set to Cvirtual 250, may be used, for example during an impedance monitoring phase, to calculate an output electrical parameter of two-port network 204, or two-port network 220, such as output voltage Vout, output current Iout, output impedance (280) and output power (Pout) that is delivered to a treated site (e.g., bodily organ, bodily tissue, etc.). However, if the parasitic capacitance of electrosurgical system 204, or of output circuitry 220, is unknown, it may be determined/found by sweeping, during a cable interrogation phase, the value of Cvirtual, and, for each value of Cvirtual, applying a voltage V1 (or Vin) and measuring an input current I1 (or Iin) to determine, or calculate, an optimal capacitance value for Cvirtual that represents, is equal to, or resembles the actual value of the parasitic capacitance. The method and process used to determine the optimal capacitance value for the virtual capacitor, Cvirtual, is described in more detail below.

Figure 3:
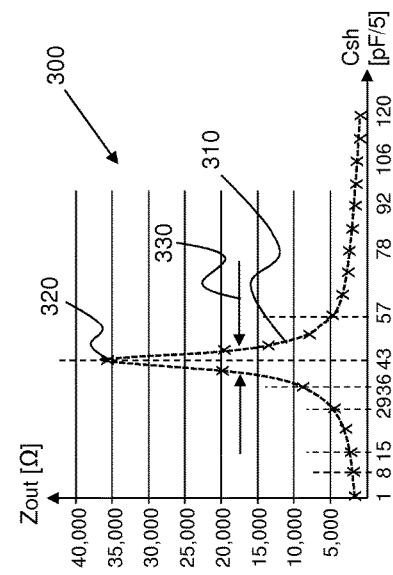
FIG. 3 shows an impedance-capacitance plot in accordance with an example embodiment.

FIG. 3 shows an example impedance-capacitance plot 300 in accordance with an example embodiment. The horizontal (X) axis of plot 300 indicates virtual capacitance values assigned/set to a virtual capacitor, Cvirtual, such as virtual capacitance 250 of FIG. 2B. The vertical (Y) axis indicates respective values of an output impedance similar to Zout 280 of FIG. 2B when the external circuit (e.g., external circuit 220 of FIG. 2B) is open; that is, when the electrosurgical system is in 'open circuit' state. (Sweeping the value of Cvirtual is to be done in the system's open circuit state in order to ensure that, for any given input voltage (Vin), the input current resulting from Vin reflects (is a function of) the leakage capacitance Clkg, or Zlkg_Ext, and is not affected by extraneous impedance (e.g., Zload; e.g., tissue's impedance, etc.).

A value of a virtual capacitor may be changed (swept) across a series of capacitance values, and an output impedance 280 may be calculated for each capacitance value from the pertinent output voltage and output current, which, in turn, are calculated by multiplying the input voltage and current by a transfer matrix, which is updated with the relevant capacitance value (Equation (19), for example, may be used to calculate an output voltage and current for each value of the virtual capacitance, Cvirtual.) Referring to example plot 310, Clkg=5 pF may result in an output impedance of approximately 2 KΩ, Clkg=135 pF may result in an output impedance of approximately 5 KΩ, Clkg=200 pF may result in an output impedance of approximately 20 KΩ, Clkg=215 pF may result in an output impedance of approximately 35 KΩ, etc.

Curve 310 may be fitted to the impedance values, and a maximum output impedance, Zmax, may be derived from curve 310 using any suitable mathematical or digital signal processing ("DSP") method. By way of example, in FIG. 3 Zmax is approximately 35 KΩ, and the capacitance value (an 'optimal capacitance value') of the virtual capacitor resulting in Zmax is approximately 215 pF. Zmax is shown as an apex 320. Apex point 320 is very conspicuous, which makes it very discernible, hence easy to detect/identify.

Sweeping of the virtual capacitor's value is to be performed when the external circuit (e.g., external circuit 220 of FIG. 2B is open (i.e., when Zload is disconnected). Therefore, curve 310 represents various open circuit conditions of (i.e., various current leakages in) the external circuit. In order to ensure that a transfer matrix genuinely represents network 204 (FIG. 2B) during an impedance monitoring phase, the capacitance value of the virtual capacitor (e.g., 215 pF in the example plot 310) in the transfer matrix, which results in the maximum output impedance (e.g., 35 KΩ, per plot 310) may be assigned/set, as an optimal capacitance value to Cvirtual during the impedance monitoring phase.

The electrical properties (e.g., impedances) characterizing circuit 204 of FIG. 2B may vary from one electrosurgical system to another and from one electrosurgical system's peripheral to another (e.g., depending on the type of the used cable(s) and/or type of therapeutic device, etc.). The electrical properties characterizing circuit 204 may change even during electrosurgical treatment, for example, due to manipulation of the system's cable(s) and therapeutic device by the surgeon. Changes in the electrical properties of circuit 204 may change the shape of the resulting Z-C curve. For example, a change in the electrical properties of circuit 200 may cause the curve to be lower (i.e., have lower impedance values) or higher (i.e., have higher impedance values), or it may cause curve apex 320 to move in one direction or another and, consequently, change the optimal capacitance value that is used during impedance monitoring phase. However, whatever the resulting Z-C curve is, its apex may remain relatively high and conspicuous. (The smaller a damping resistance in circuit 204 of FIG. 2B (i.e., the less lossy the circuit), the higher the circuit's Q factor and, consequently, the narrower the spike width (e.g., spike width 330), which makes the curve apex conspicuous.) Since the impedance of a tissue is mostly resistive, it has only little effect, if any, on the location of the curve's apex on the capacitance axis, hence on the value of the virtual capacitance resulting in the maximum output impedance (Zmax).

By repeating the cable interrogation process described herein, say, once in a while (e.g., once every few minutes), or based on a predefined criteria (e.g., an instantaneous output impedance sensed exceeding a threshold value; e.g., 10 KΩ) a new graph/plot may be calculated or fitted to accommodate for changes in the electrical properties of/in any part of circuit 204 of FIG. 2B and from which corresponding virtual capacitance may be selected. For example, when a cable connected to an electrosurgical system is replaced with a different type or model of cable and/or when the type of therapeutic device connected to the cable is replaced with a different type of therapeutic device, the elements of the transfer matrix B (see, e.g., formula (23) above) may be updated according to the electrical parameters of the new cable and therapeutic device (e.g., using relevant information in their manuals or specification sheet, etc.). Then, a new cable interrogation process may be initiated, by using the updated transfer matrix, to find a new capacitance value that is suitable for use with the new cable and/or therapeutic device. Then, the transfer matrix with/ including the new capacitance value may be used to monitor an electrosurgical system's output electrical parameter (e.g., output voltage, output current, output impedance, output electrical power), during an impedance interrogation phase, as described herein.

Figure 4:
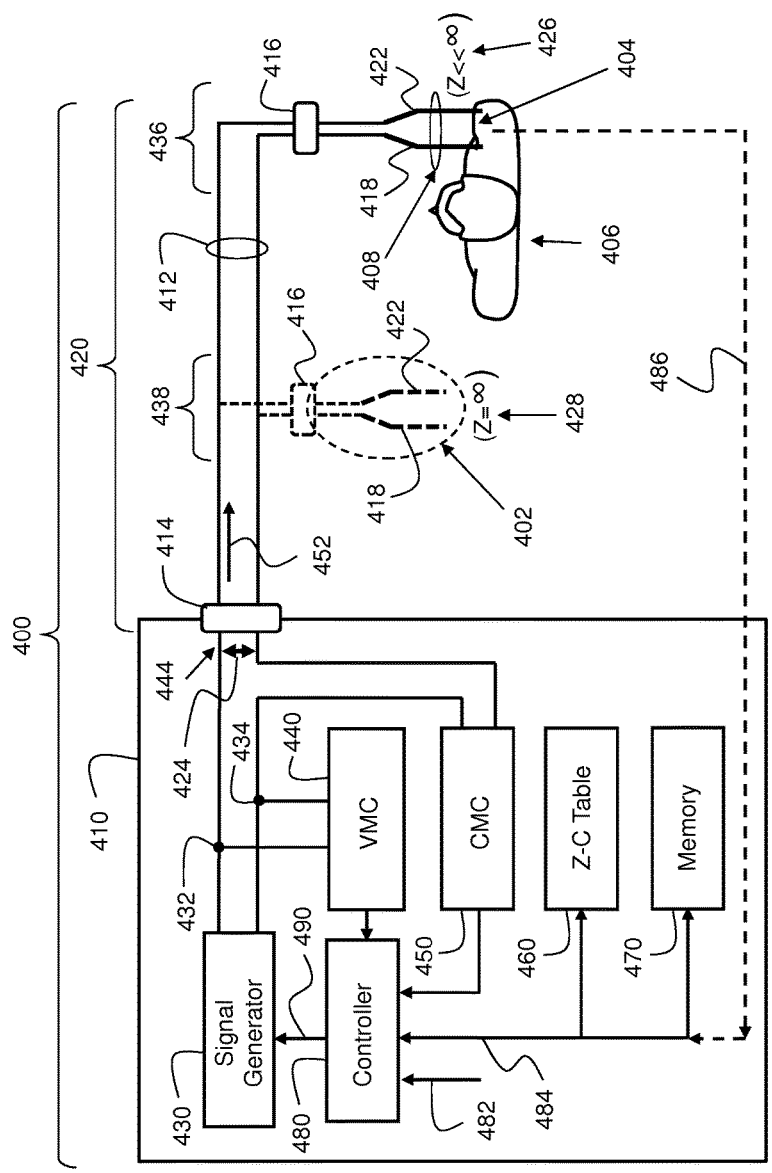
FIG. 4 is a block diagram of an electrosurgical system and setup and setting according to an example embodiment.

FIG. 4 is a block diagram of a system 400 for treating a bodily organ or tissue according to an example embodiment. System 400 may include an electrosurgical system 410 and an output circuitry 420 connectable to electrosurgical system 410.

Electrosurgical unit 410 may include a signal generator 430 (e.g., RF signal generator) for generating, among other things, low energy impedance interrogation signals, for example less than 1 watt, for example at a frequency of 80 kHz, for example, during an impedance monitoring/interrogation phase. Signal generator 430 may also generate similar low energy signals during a cable interrogation phase. Signal generator 430 may also generate high energy (e.g., 1-70 watt) RF therapeutic signal that electrosurgical system 410 may deliver, during an electrosurgical procedure, to a bodily organ or tissue (e.g., electrosurgical site 404) of a subject 406 via, through or using output circuitry 420. Electrosurgical system 410 may also include a voltage monitoring circuit ("VMC") 440, a current monitoring circuit ("CMC") 450, an impedance-capacitance (Z-C) table 460 and a memory 470.

Output circuitry 420 of electrosurgical system 410 may include a therapeutic electrosurgical device 402 via/by which electrosurgical system 410 may deliver RF therapeutic energy from RF signal generator 430 to bodily organ, or tissue, 404 of subject 406 in, or during, a closed circuit state (of electrosurgical system 410 or output circuitry 420) in which therapeutic device 402 closes an output 'port' 408 of output circuitry 420 via bodily organ/tissue 404. Output circuitry 420 may also include a cable system for connecting therapeutic device 402 to electrosurgical system 410. The cable system may include at least a cable 412, a connector or adapter 414 via which cable 412 may be connected to electrosurgical system 410, and a connector or adapter 416 via which cable 412 may be connected to electrosurgical device 402. Electrosurgical device 402 may be or include a bipolar instrument/tool including two electrode tines (418, 422) for performing various surgical operations, for example coagulation, ablation, cutting and/or other operations.

Electrosurgical device 402 may, at times (e.g., occasionally, intentionally, unintentionally), touch bodily organ or tissue 404, in which case electrosurgical system 410 may sense (at 424), through electrode tines 418 and 422 (that make up, or form, output port 408 of output circuit 420), an output impedance, Zout, which is, or represents, the tissue's impedance (426) or approximately the tissue's impedance, which may be relatively low (e.g., a few ohms to a few kilo ohms). A system state where electrosurgical device 402 touches bodily organ or tissue 404, which results in a relatively low output impedance, Zout, as may be sensed, for example, by electrosurgical system 410 at 424, is referred to herein as a 'closed circuit' state of electrosurgical system 410 or output circuitry 420 of electrosurgical system 410.

Electrosurgical device 402 may, at other times, not touch bodily organ or tissue 404, in which case electrosurgical system 410 is to, theoretically, sense (at 424) an output impedance, Zout, that is infinitely high (428). A system state where electrosurgical device 402 does not touch bodily organ or tissue 404, which should theoretically result in a relatively very high output impedance, Zout, as may be sensed, for example, by electrosurgical system 410 at 424, is referred to herein as an 'open circuit' state of electrosurgical system 410 or output circuitry 420 of electrosurgical system 410. However, in practice, due to parasitic (leakage) capacitances due to or caused by, for example, cable 412, connectors/adapters 414 and 416 and/or by electrosurgical device 402 and/or by additional circuit elements (e.g., gripping the electrosurgical device by a surgeon), the output impedance, Zout, that electrosurgical system 410 may sense at 424 is, or can be, in the order of the tissue's impedance.

Controller 480 may receive (e.g., from a user; e.g., surgeon, operating the system) an input signal or message 482 instructing controller 480 to operate electrosurgical system 410 in a cable interrogation mode during a cable interrogation phase, or in an impedance interrogation mode during an impedance monitoring phase, or in RF therapeutic energy delivery mode during therapeutic RF energy delivery phase. (Controller 480 may, in the RF therapeutic energy delivery mode, cause RF generator 430 to generate RF therapeutic energy, and it may cause electrosurgical system 410 to deliver the RF therapeutic energy to organ/tissue 404.) Alternatively or additionally, controller 480 may determine when each operation mode should be activated, deactivated, resumed, etc. based on signal or message it may receive from either VMC 440 or CMC 450, or from both monitoring circuits.

After cable 412 and electrosurgical device 402 are connected to system 410), controller 480 may perform a cable interrogation process in order to find an optimal capacitance value that is suitable for (e.g., represents, or is equal or similar to the leakage capacitances caused by) the particular cable and therapeutic device 402.

Controller 480 may, during or for the cable interrogation phase, define a transfer matrix for output circuit 420 when output circuitry 420 is open (e.g., when therapeutic device 402 is detached from organ/tissue 404), and store the transfer matrix, for example, in memory 470. The transfer matrix may include a virtual capacitor, and controller 480 may change the value of the virtual capacitor in order to change the output impedance, Zout, of output circuitry 420 in order to identify a maximum output impedance (Zmax). That is, during the cable interrogation process, controller 480 may (virtually) sweep the value of the virtual capacitor, Cvirtual, and, for each selected value of Cvirtual, controller 480 may calculate an output impedance, Zout, for that value by using the transfer matrix. Controller 480 may, then, update the matrix information, which may be stored, for example, in memory 470, with the value of the virtual capacitance.

During the cable interrogation phase, controller 480 may store, for example in Z-C table 460, capacitance values it selects for the virtual capacitance and also output impedances that controller 480 respectively calculates for these capacitance values. After controller 480 selects/uses up, and stores, all the virtual capacitance values to be selected/used, controller 480 may identify an output impedance having the greatest value as the maximum output impedance, Zmax, and determine the associated (i.e., related optimal) virtual capacitance that controller 480 may use during the impedance interrogation phase. (Controller 480 may select Zmax from the stored output impedances, or it may interpolate it from the stored output impedances.)

Controller 480 may be configured to, during the impedance interrogation phase, monitor an instantaneous output electrical parameter of output circuitry 420 (e.g., voltage, current, impedance, electrical power delivered to the treated site) by/while using the optimal capacitance value. (The 'optimal capacitance value' is the capacitance value assigned to the virtual capacitance, which result in the maximum output impedance, Zmax.) Using the optimal capacitance value, which may change from one cable interrogation to another, enables controller 480 to determine, for example, the instantaneous output impedance and/or output electrical power of the output circuitry accurately and reliably. Using the optimal capacitance value also enhances the controller 480 ability to distinguish between the closed circuit state (in which controller 480 switches (490) signal generator 430 on) and the open circuit state of electrosurgical system 410, or output circuitry 420 (in which controller 480 switches (490) signal generator 430 off). Controller 480 may also use the output electrical power to control (490) signal generator 430, for example, such that the therapeutic energy delivered to the treated site during therapy is optimal throughout the therapeutic procedure.

During the impedance interrogation phase, controller 480 may calculate the system's instantaneous output impedance, Zout, resulting, for example, from the cable (e.g., 412), cable connectors (e.g., 414, 416), cable adapters, therapeutic device (402), and bodily organ/tissue 404 (if therapeutic device 402 touches bodily organ/tissue 404) by outputting, or applying, an interrogation voltage, Vin, between terminals 432 and 434 (and measuring that voltage by VMC 440), and concurrently measuring the resulting interrogation current Iin (452) by CMC 450. Then, controller 480 may multiply voltage Vin and the measured current Iin by the transfer matrix, in which the optimal capacitance value is set to the virtual capacitor, to obtain a corresponding output voltage (Vout) and output current (Iout) at the electrosurgical device's electrode tines 408. Controller 480 may calculate the output impedance Zout (Zout=Vo/Io) and, based on its value, determine the next operation mode of electrosurgical system 410. 'Knowing' the output voltage (Vout) and output current (Iout) at the electrode tines 408, controller 480 may also determine the therapeutic energy actually delivered to the treated site. Knowing the actual therapeutic energy delivered to the treated site, controller 480 may control (490) the operation of signal generator 430 (e.g., it may control an electrical parameter of the generator) to deliver an optimal amount of therapeutic energy to the treated site at any given time during the RF therapeutic delivery phase.

Signal Generator 430 may controllably deliver therapeutic RF energy to a treated site. When signal Generator 430 is not delivering therapeutic RF energy, it may deliver, at times, a relatively small average interrogation current 452 (e.g., in the order of micro amps), for example in compliance with IEC safety regulations, to interrogate or sense the presence and magnitude of a tissue impedance.

Figures 5, 6:
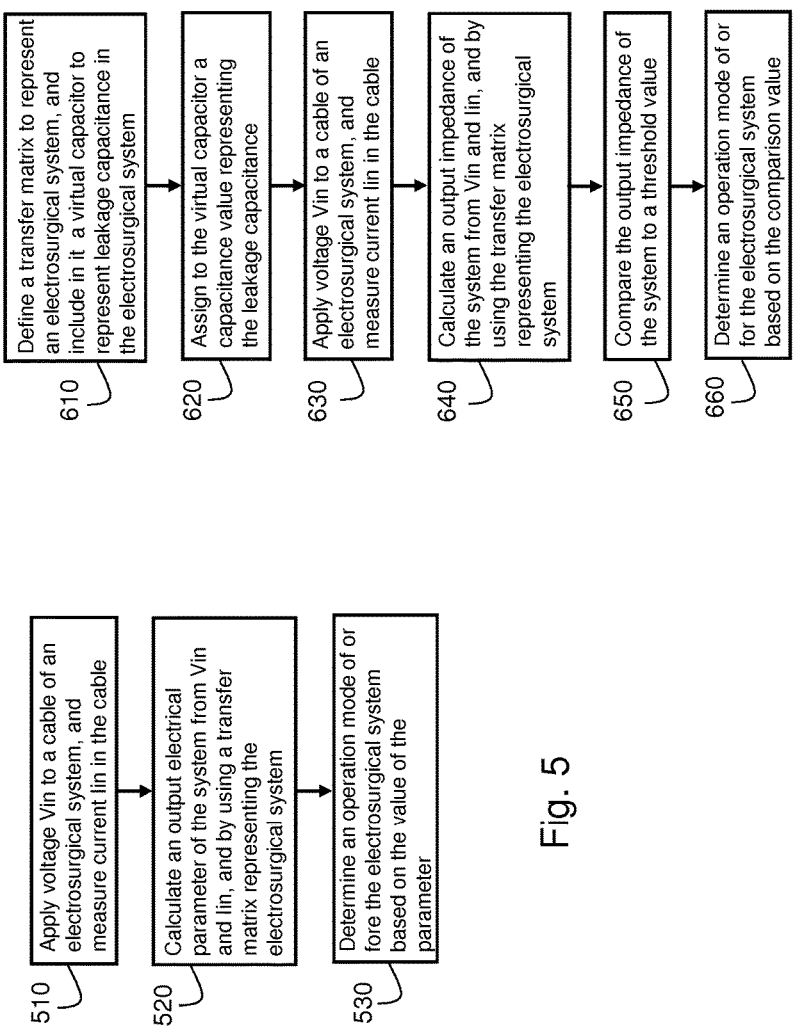
FIG. 5 shows a method of operating an electrosurgical system according to an example embodiment.
FIG. 6 shows a method of operating an electrosurgical system according to another example embodiment.

FIG. 5 shows a method of operating an electrosurgical system (e.g., system 400 or system 410, FIG. 4) according to an example embodiment. Assume that the electrosurgical system is connected to, or include, a signal generator (e.g., signal generator 430, FIG. 4) and an output circuitry (e.g., output circuitry 420, FIG. 4) including an electrical cable (e.g., cable 412, FIG. 4) connecting an electrosurgical device (e.g., signal generator 402, FIG. 4) to the electrosurgical system. At step 510, apply or provide an input voltage (Vin) to the electrical cable, and concurrently measure an input current (Iin) in the electrical cable in response to Vin.

At step 520, calculate an electrical parameter of the output circuitry from the input voltage (Vin) and the input current (Iin) and by using a transfer matrix electrically representing the output circuitry. The electrical parameter of the output circuitry may be selected from the group consisting of output voltage, output current, output impedance and output electrical power that is delivered to the treated site. In case the electrical parameter is an output impedance of the output circuitry, the method may include determining the operation mode of or for the electrosurgical system based on a value of the output impedance, and/or distinguishing, based on the value of the output impedance, between an 'open circuit' state of the output circuitry in which the electrosurgical device is detached, or removed, from a treated site, and a 'closed circuit' state of the output circuitry in which the electrosurgical device touches the treated site. The value of the output impedance of the output circuitry may be determined in the way described herein.

In case the electrical parameter is an output electrical power delivered via the output circuitry to the treated site, the method may include calculating an output voltage (Vout) and an output current (Iin) of the output circuitry by multiplying Vin and Iin by the transfer matrix. The method may further include controlling the output electrical power to provide an optimal therapeutic energy to the treated site.

At step 530, determine an operation mode of or for the electrosurgical system based on the value of the electrical parameter. The operation mode may be selected from the group consisting of: (i) delivering, by a signal generator (e.g., signal generator 430, FIG. 4), via the electrosurgical device, therapeutic energy to a treated site, (ii) adjusting an electrical parameter of the signal generator when the therapeutic energy is delivered to the treated site, (iii) refraining from delivering therapeutic energy to the treated site, (iv) cable interrogation mode and (v) impedance monitoring mode.

FIG. 6 shows a method of operating an electrosurgical system according to an example embodiment. In general, the method includes steps implementing, or used during, a cable interrogation phase during which a capacitance value representing leakage capacitance in the electrosurgical system may be selected for use in a transfer matrix that represents the electrosurgical system, or part thereof, including the system's parasitic capacitance. The method may also include steps implementing, or used during, an impedance monitoring phase during which the electrosurgical system may use the selected capacitance value representing the leakage capacitance in the electrosurgical system to monitor the instantaneous an output impedance of the electrosurgical system. Steps 610 and 620 (inclusive) are directed to the cable interrogation phase. Steps 630 through 660 are directed to the impedance interrogation/monitoring phase.

Assume that the electrosurgical system includes, or is connected to, an output circuitry comprising an electrical cable connected to an electrosurgical device.

At step 610, defining a transfer matrix, the transfer matrix electrically representing the output circuitry and comprising a virtual capacitor (Cvirtual) to represent a leakage capacitance (Clkg) in the output circuitry, and at step 620, assign to the virtual capacitor (Cvirtual) a capacitance value representing the leakage capacitance (Clkg). The way the capacitance value to be assigned or set to the virtual capacitor (Cvirtual) is selected is described herein. For example, the capacitance value may be obtained automatically (e.g., by reading it from an external device associated with the cable; e.g., from an RFID tag or a barcode, or through sweeping of the capacitance value of the virtual capacitance, as described herein) or manually.

Steps 630 through 660 may be performed during an electrosurgical procedure (e.g., during an impedance monitoring phase). At step 630, apply or provide, by the electrosurgical system, an input voltage (Vin) to the electrical cable and measure an input current (Iin) in the electrical cable. At step 640, calculate an output impedance (Zout) of the output circuitry from the input voltage (Vin) and the input current (Iin), and by using the transfer matrix, and, at step 650, compare the output impedance (Zout) to an impedance threshold value. Comparing the output impedance of the system to a threshold value may include determining, based on the impedance comparison result, whether the output circuitry is in an 'open circuit' state in which the electrosurgical device does not touch a bodily organ or tissue, or in a 'closed circuit' state in which the electrosurgical device touches the bodily organ or tissue.

At step 660, determine an operation mode of the electrosurgical system based on the comparison result. Determining an operation mode of the electrosurgical system may include, for example, determining whether the electrosurgical device is connected to the electrical cable, or whether the electrosurgical device touches a treated site. (Other or additional operation modes may be determined or use, as exemplified herein.)

The output impedance (Zout) of the electrical cable may be found in the way described herein, for example it may be found by calculating, by using the transfer matrix, an output voltage (Vout) and an output current (Iout) for the output circuitry from the input voltage (Vin) and from the input current (Iin), etc. The output voltage (Vout) and output current (Iout) may additionally or alternatively be used to calculate an electrical power (Pout) that is delivered to a treated site from the electrosurgical system via the electrosurgical device.

Figure 7:
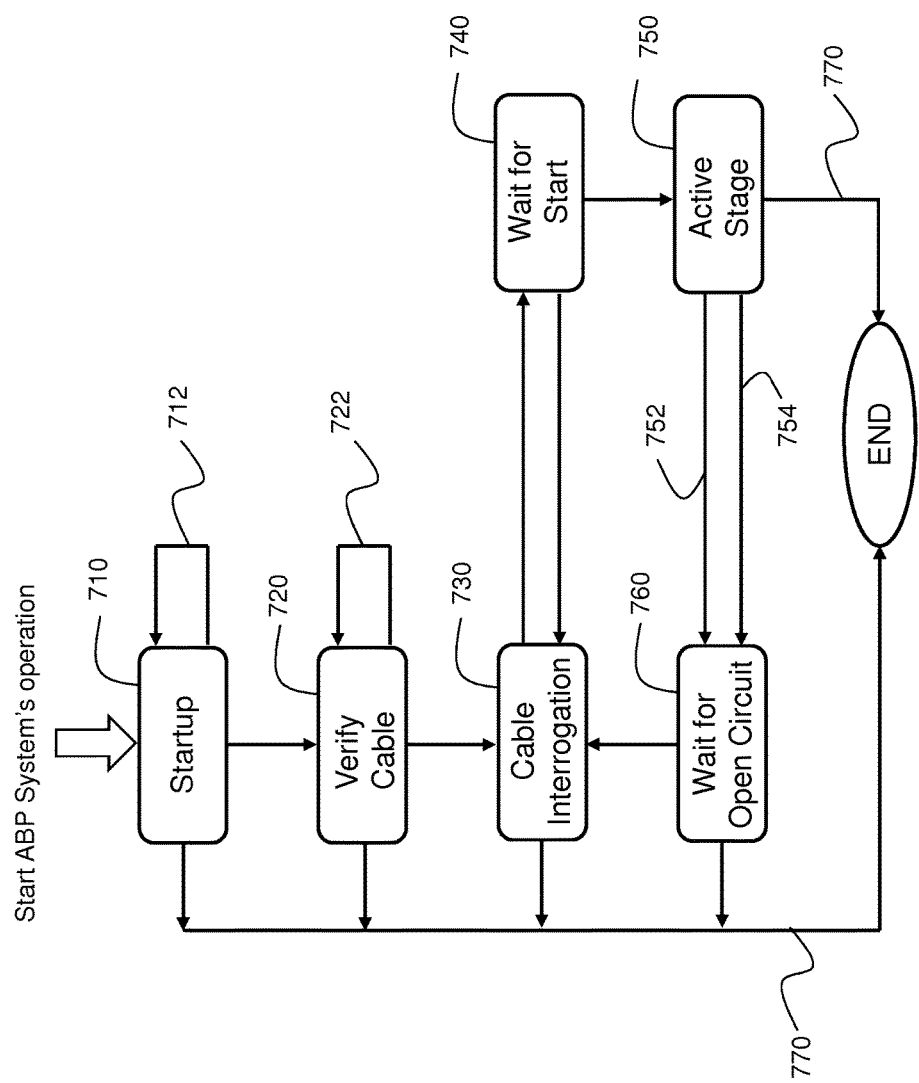
FIG. 7 shows a block diagram demonstrating usage of the methods disclosed herein by an electrosurgical system according to an example embodiment.

FIG. 7 shows a block diagram demonstrating usage of the methods disclosed herein by an electrosurgical system according to an example embodiment. Initially, a cable and therapeutic device are connected to an electrosurgical system, and default cable compensation parameters may be used. (The term 'cable compensation parameters' refer to a transfer matrix representing the electrosurgical system, or part thereof; e.g., an output circuitry connected to the electrosurgical system.)

At block or condition 710 ("Startup") the electrosurgical system checks whether a cable is connected to it, and, if a cable is connected to it, whether the connection is intact. Since at this stage the generator delivering therapeutic energy is shut down (switched off), it is expected that the output impedance, Zout, which is calculated by the electrosurgical system during the cable interrogation phase disclosed herein, should be greater than a first predetermined impedance threshold value (Zmin), for example Zout should be greater than, say, Zmin=800 ohms. (Other threshold values may be used.) If Zout is lower than the threshold value (Zout<Zmin), the electrosurgical system may wait a predetermined time period (712), and if Zout, which the electrosurgical system repeatedly calculates, remains lower than Zmin for a period that is longer than the predetermined time period, the electrosurgical system may indicate this condition ('Zout too low') to the operator and abort operation, because this condition may indicate, for example, a faulty cable. However, if, Zout>Zmin during the predetermined time period, the electrosurgical system may assume that a cable is connected to the electrosurgical system and, accordingly, cancel the 'Zout too low' indication, and it may continue to block or condition 720 ("Verify Cable").

At block or condition 720 the electrosurgical system may check, for example based on Zout, whether the electrosurgical system is in 'open circuit' state, that is, whether the cable (and possibly the electrosurgical device) are ready for use. If Zout is lower than a second impedance threshold value Zopen (e.g., Zopen=10 KΩ. Other threshold values may be used), it may be assumed that there may be a problem with the cable, or electrosurgical device, or both. Therefore, the electrosurgical system may wait a predetermined time period (at 722), and if Zout<Zopen for more than the specified time period, the electrosurgical system may indicate this condition ('Cable not detected'), for example to the operator, and abort operation, because it may be that no cable is connected to the electrosurgical system, or that the cable was disconnected, for example unintentionally, or that not all cable wires are properly connected. However, if, Zout>Zopen, the electrosurgical system may cancel the 'Cable not detected' indication, and continue to block 730 ("Cable Interrogation") to initiate a cable interrogation phase.

At block or condition 730 the electrosurgical system continues to monitor the system's output impedance in order to determine whether therapeutic energy can be delivered to a treatment site. The electrosurgical system may use a third impedance threshold value, Zstart (e.g., Zstart=2.2 KΩ. Other threshold values may be used; e.g., 2.5 KΩ), by the electrosurgical system to determine when it can deliver therapeutic energy to the treated site. If the condition Zout<Zstart is met, the electrosurgical system may move on (732) to block or condition block 740 ("Wait for Start"), where a delay timer may be activated. If the condition Zout<Zstart is met uninterruptedly for a period of time (which may be, for example, between 0 seconds and 2.5 seconds) that may be set by block 740, this means that the electrosurgical device has not touched the treated site by accident but, rather, the system operator is ready to start, or resume, therapy. Therefore, the (current) cable interrogation session can be terminated, at least temporarily, and therapeutic energy can be generated and delivered (744) through the electrosurgical device. Otherwise (i.e., if Zout is not lower than Zstart for the specified time period), cable interrogation condition may be resumed (742).

At block or condition 750 ("Active Stage") the electrosurgical system delivers therapeutic energy to the treated site. Block 750 may be exited in one of three ways: (1) the operator of the electrosurgical system may decide to abort (770) the electrosurgical procedure, or (2) after a timeout is indicated (752), or (3) when Zout is greater than a third impedance threshold value, Zstop (754) (e.g., Zstop=3.5 KΩ). (Other threshold values may be used.) If timeout is reached, this means that the electrosurgical device should be removed from the treated site in order not to overheat the treated tissue/organ. If Zout>Zstop, this means that the electrosurgical system should stop delivering therapeutic energy delivery, and commence a new cable interrogation session. In both cases (2) and (3) the electrosurgical system waits, in block 760 ("Wait for Open Circuit"), for the operator to move the electrosurgical device away from the treated site, that is, it continues to monitor the output impedance and waits until Zout>Zopen. Then, electrosurgical system may revisit block 730 and repeat the process as described above.

Figure 8:
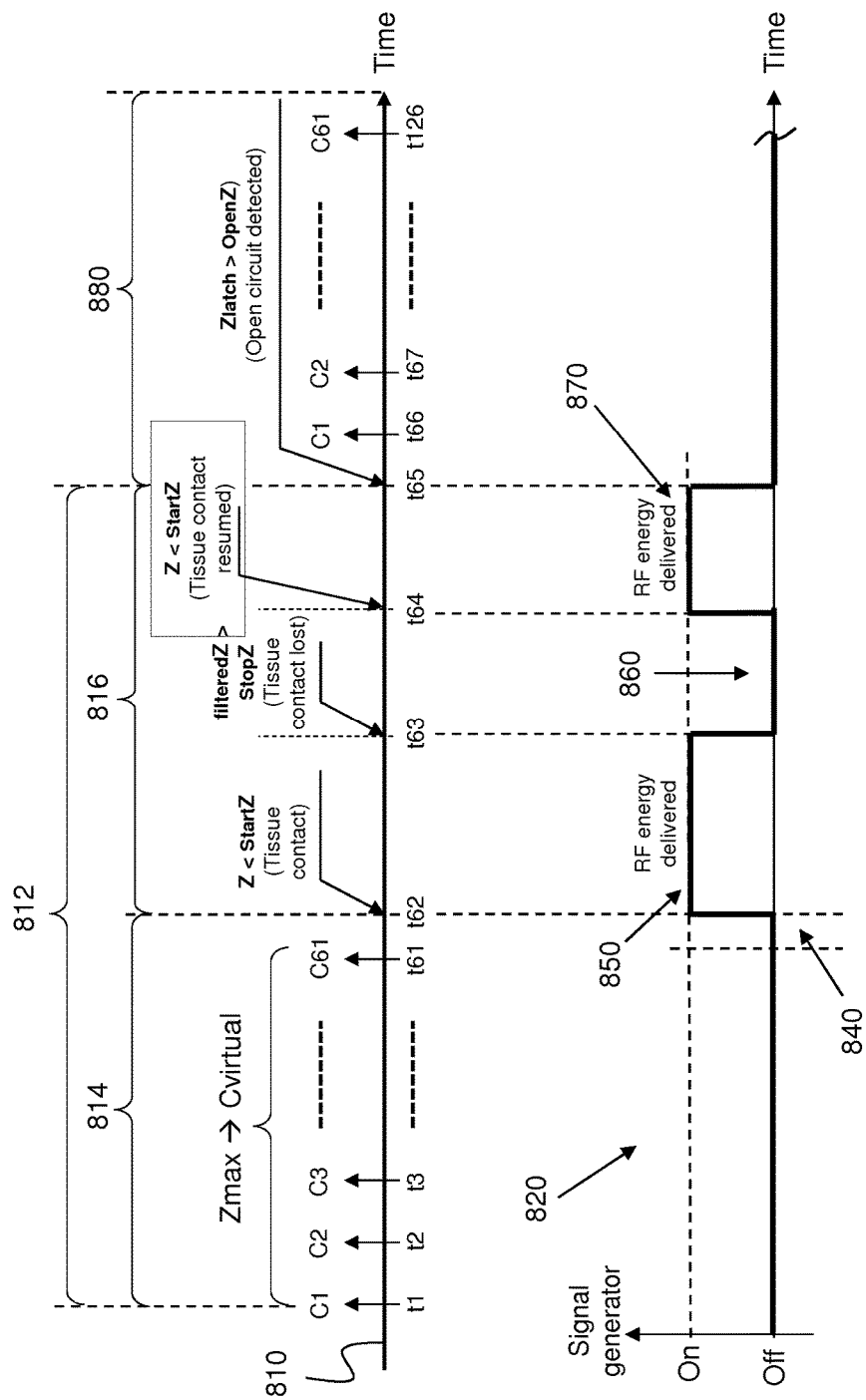
FIG. 8 schematically illustrates utilization of methods according to an example embodiment.

FIG. 8 schematically illustrates utilization of methods according to an example embodiment. Various events occurring in an electrosurgical system are chronologically shown with respect to timeline 810. Graph 820 illustrates a status of a signal generator (e.g., signal generator 430, FIG. 4) generating, at times, high energy therapeutic signal, and, at other time, lower energy therapeutic signal.

With reference to timeline 810, an electrosurgical system's operation cycle 812 may include a cable interrogation period 814, to obtain a capacitance value representing leakage capacity of an electrosurgical system, or part thereof, and a period 816 during which the electrosurgical system's instantaneous output impedance is monitored (interrogated) by using the result of the cable interrogation result; i.e., by using a transfer matrix that electrically represents the electrosurgical system, or part thereof, and includes the capacitance value representing the leakage capacitance in, or of, the electrosurgical system, or part thereof.

During cable interrogation period 814, a capacitance value C1 (e.g., C1=50 pF) is assigned, at time t1, to a virtual capacitor in the transfer matrix, and a corresponding output impedance Zout(1) is calculated for C1. At time t2, a capacitance value C2 (e.g., C1=60 pF) is assigned to the virtual capacitor, and a corresponding output impedance Zout(2) is calculated for C2, and so on (for C3 through C61 at time t61). A maximum output impedance, Zmax, is derived from the series of impedances Zout(1)-Zout(61), and an optimal capacitance value, which is a capacitance value resulting in Zmax, may be determined. The optimal capacitance value may, then, be assigned or set to the virtual capacitor, Cvirtual, and interrogation of the electrosurgical system's output impedance (or any other output electrical parameter) may commence.

Between times t61 and t62 a first interrogation period 840 is initiated. According to the example of FIG. 8, at time t62 it may be determined that the therapeutic device controlled by the electrosurgical system touches an organ or tissue. (The determination may be made if the value of the monitored output impedance is, in this example, lower than a 'start impedance', Zstart, threshold value that may be, for example, 2.2 KΩ) Therefore, the signal generator may start delivering therapeutic energy (850) to the tissue at time t62. At time t63, it is determined that the therapeutic device does not touch the organ or tissue. (The determination may be made if the value of the monitored instantaneous output impedance is, in this example, greater than a 'stop impedance', Zstop, threshold value that may be, for example, 3.5 KΩ) Therefore, the signal generator stops delivering the therapeutic energy (860) to the tissue at time t63.

At time t64, tissue contact is detected again (through monitoring of the instantaneous output impedance). (The determination is made if the value of the monitored instantaneous output impedance is, again, lower than the start impedance threshold value, Zstart.) Therefore, the signal generator restarts delivering therapeutic energy (870) to the tissue at time t64.

At time t65 it is determined that the instantaneous output impedance indicates that the electrosurgical system's output impedance is in open state, in which condition another cable interrogation process 880 may commence, for example, to find a more suitable capacitance value for the virtual capacitor. ('More suitable' means able to accommodate for a change in the electrical properties (e.g., leakage impedances) of the electrosurgical system, or part thereof).

During period 816, a series of interrogation periods may be used to monitor the electrosurgical system's instantaneous output impedance. Interrogation of an instantaneous output impedance may be performed during a period when the signal generator does not deliver therapeutic energy. That is, delivering of the therapeutic energy to an organ or tissue may be pulsed (e.g., in bursts), and the interrogation of the instantaneous output impedance may be performed in-between such pulses/bursts.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Embodiments of the invention may include a computer or processor non-transitory storage medium, such as for example a memory, a disk drive, or a USB flash memory, encoding, including or storing instructions, e.g., computer-executable instructions, which when executed by a processor or controller, carry out methods disclosed herein. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of electrosurgical systems (e.g., auto bipolar type electrosurgical systems, monopolar type electrosurgical systems, etc.), to various types of cables (e.g., auto bipolar cables, etc.), and to various types of electrosurgical devices. Hence the scope of the claims that follow is not limited by the disclosure herein to any particular electrosurgical system or electrosurgical device.

The invention claimed is:

1. A method of operating an electrosurgical system connected to an output circuitry comprising an electrical cable connected to an electrosurgical device, the method comprising: defining a transfer matrix, the transfer matrix electrically representing the output circuitry and including a virtual capacitor; assigning to the virtual capacitor a capacitance value during a cable interrogation phase, wherein the cable interrogation phase includes: changing the capacitance value of the virtual capacitor across a series of capacitance values; calculating, by using the transfer matrix, for the output circuitry, a series of output impedances respectively corresponding to the series of capacitance values; deriving a maximum output impedance from the series of output impedances; and determining the capacitance value for the virtual capacitor (Cvirtual) for which output impedance is maximal; applying, by the electrosurgical system, an input voltage to the electrical cable and measuring an input current in the electrical cable; calculating an output impedance of the output circuitry from the input voltage and the input current using the transfer matrix; and comparing the output impedance to an impedance threshold value; and determining an operation mode of the electrosurgical system based on a comparison result.

2. The method as in claim 1, wherein calculating the output impedance of the output circuitry comprises calculating, by using the transfer matrix, an output voltage and an output current for the output circuitry from the input voltage and from the input current.

3. The method as in claim 2, further comprising calculating, from the output voltage and output current, an electrical power delivered to a bodily organ or tissue from the electrosurgical system via the electrosurgical device.

4. The method as in claim 1, comprising, while the electrosurgical device is disconnected from the electrical cable:
applying, by the electrosurgical system, the input voltage to the electrical cable and measuring the input current in the electrical cable in response to the applied input voltage; and
for each value of the virtual capacitor:
multiplying the input voltage and the input current by the transfer matrix to obtain an output voltage and an output current for the output circuitry; and
calculating the output impedance of the output circuitry from the output voltage and the output current.

5. The method as in claim 1, comprising selecting the maximum output impedance from the series of output impedances.

6. The method as in claim 1, comprising interpolating the maximum output impedance from the series of output impedances.

7. The method as in claim 1, comprising changing the value of the virtual capacitor according to a capacitance interval.

8. The method as in claim 1, comprising changing the value of the virtual capacitor within a capacitance range 50 pF-600 pF.

9. The method as in claim 1, wherein determining an operation mode of the electrosurgical system comprises determining whether the electrosurgical device is connected to the electrical cable.

10. The method as in claim 1, wherein determining an operation mode of the electrosurgical system comprises determining whether the electrosurgical device touches a bodily organ or tissue.

11. The method as in claim 1, further comprising determining, based on the comparison result, whether the output circuitry is in an 'open circuit' state in which the electrosurgical device does not touch a bodily organ or tissue, or in a 'closed circuit' state in which the electrosurgical device touches the bodily organ or tissue.

12. The method as in claim 1, wherein the output circuitry comprises any of: (i) the electrical cable connected to the electrosurgical system, (ii) an adapter connecting the electrical cable to the electrosurgical system, and (iii) an adapter connecting the electrosurgical device to the electrical cable, including any combination thereof.

* * * * *